US009540478B2

(12) United States Patent
Moore et al.

(10) Patent No.: US 9,540,478 B2
(45) Date of Patent: *Jan. 10, 2017

(54) BIODEGRADABLE POLYURETHANE AND POLYURETHANE UREAS

(71) Applicant: Polynovo Biomaterials Pty Limited, Clayton (AU)

(72) Inventors: Timothy G. Moore, Surrey Hills (AU); Raju Adhikari, Wheelers Hill (AU); Pathiraja Arachchillage Gunatillake, Mulgrave (AU)

(73) Assignee: POLYNOVO BIOMATERIALS PTY. LIMITED, Clayton, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/685,837

(22) Filed: Apr. 14, 2015

(65) Prior Publication Data

US 2015/0246994 A1 Sep. 3, 2015

Related U.S. Application Data

(63) Continuation of application No. 11/087,561, filed on Mar. 24, 2005, now Pat. No. 9,034,378.

(30) Foreign Application Priority Data

Mar. 24, 2004 (AU) ................................ 2004901576

(51) Int. Cl.
*A61L 27/18* (2006.01)
*C08G 18/34* (2006.01)
(Continued)

(52) U.S. Cl.
CPC ........... *C08G 18/348* (2013.01); *A61K 31/785* (2013.01); *A61L 27/18* (2013.01); *A61L 27/3804* (2013.01);
(Continued)

(58) Field of Classification Search
CPC ..... C08G 18/348; C09D 175/06; A61L 27/18; A61L 27/3804; A61L 31/10; A61L 27/54; A61L 2300/412; A61L 2300/414
See application file for complete search history.

(56) References Cited

U.S. PATENT DOCUMENTS 6,221,997 B1 * 4/2001 Woodhouse ........... C08G 18/12
528/61
6,372,876 B1 4/2002 Kim et al.
(Continued)

FOREIGN PATENT DOCUMENTS

CA 2219545 A1 4/1999
WO WO-8905830 A1 6/1989
(Continued)

OTHER PUBLICATIONS

Gorna, Katarzyna, et al., Synthesis and Characterization of Biodegradable Poly (?-caprolactone urethans)s. Effect of the Polyol Molecular Weight, Catalyst, and Chain Extender on the Molecular and Physical Characteristics.
(Continued)

*Primary Examiner* — Michael L Leonard
(74) *Attorney, Agent, or Firm* — Polsinelli PC

(57) ABSTRACT

This invention relates to biocompatible, biodegradable thermoplastic polyurethane or polyurethane/ureas comprising isocyanate, polyol and a conventional chain extender and/or a chain extender having a hydrolysable linking group and their use in tissue engineering and repair applications, particularly as stents and stent coating.

17 Claims, 11 Drawing Sheets

(51) Int. Cl.

| | |
|---|---|
| *A61K 31/785* | (2006.01) |
| *A61L 31/10* | (2006.01) |
| *C08G 18/32* | (2006.01) |
| *C08G 18/42* | (2006.01) |
| *C08G 18/66* | (2006.01) |
| *C08G 18/77* | (2006.01) |
| *A61L 27/38* | (2006.01) |
| *A61L 27/54* | (2006.01) |
| *C09D 175/06* | (2006.01) |

(52) U.S. Cl.
CPC ............... *A61L 27/54* (2013.01); *A61L 31/10* (2013.01); *C08G 18/3206* (2013.01); *C08G 18/3221* (2013.01); *C08G 18/4277* (2013.01); *C08G 18/6607* (2013.01); *C08G 18/771* (2013.01); *C09D 175/06* (2013.01); *A61L 2300/412* (2013.01); *A61L 2300/414* (2013.01); *C08G 2230/00* (2013.01)

(56) References Cited

U.S. PATENT DOCUMENTS

| | | |
|---|---|---|
| 6,376,742 B1 | 4/2002 | Zdrahala et al. |
| 6,627,258 B1 | 9/2003 | Flodin et al. |
| 6,869,999 B2 | 3/2005 | Kaufhold et al. |
| 2001/0043913 A1 | 11/2001 | Spaans et al. |
| 2002/0035231 A1 | 3/2002 | Whitehouse et al. |
| 2005/0238683 A1 | 10/2005 | Adhikari et al. |

FOREIGN PATENT DOCUMENTS

| | | |
|---|---|---|
| WO | WO-9322360 A1 | 11/1993 |
| WO | WO-0067812 A1 | 11/2000 |
| WO | WO-2004029123 A1 | 4/2004 |

OTHER PUBLICATIONS

General Concepts of Biocompatibility. Williams, D.F. Handbook of Biomaterial Properties. 1998, 481-488.

* cited by examiner

BIODEGRADABLE POLYURETHANE AND POLYURETHANE UREAS

CROSS-REFERENCE TO RELATED APPLICATIONS

This Application is a Continuation of application Ser. No. 11/087,561 filed on Mar. 24, 2005. Application Ser. No. 11/087,561 claims priority to Australian Application No. 2004901576, filed on Mar. 24, 2004, the entire contents of which is hereby incorporated by reference.

FIELD OF THE INVENTION

The present invention relates to biodegradable processable and preferably thermoplastic polyurethanes or polyurethane/ureas and processes for their preparation. The polymers are biodegradable, processable and preferably thermoplastic which makes them useful in biomedical applications including, for example, in the fabrication of scaffolds for tissue engineering applications. The invention particularly relates to the use of such polyurethanes and polyurethane/ureas in fabricating scaffolds using rapid prototyping techniques.

BACKGROUND TO THE INVENTION

Biodegradable synthetic polymers offer a number of advantages over other materials in various biological applications including tissue repair. For example, in relation to the development of scaffolds in tissue engineering, the key advantages include the ability to tailor mechanical properties and degradation kinetics to suit various applications. The simple and routine fabrication of scaffolds with a size and shape similar to organs or parts of organs would, for example, help tissue engineering technology to develop such organs in vivo or in vitro using bioreactors. Likewise, scaffolds with appropriate mechanical properties can be fabricated and implanted in the body to help repair damaged tissues such as those in coronary arteries and other blood vessels. For example, biodegradable scaffolds fabricated as coronary stents can support the vessel during the healing process and degrade and be released from the body after the vessel is repaired.

Synthetic polymers are also attractive in tissue engineering applications because they can be fabricated into various shapes with desired pore morphologic features conducive to tissue in-growth. Furthermore, polymers can be designed with chemical functional groups that can, for example, induce tissue in-growth, or be utilised to adapt the polymers to the application in question.

A vast majority of biodegradable polymers studied in these fields belong to the polyester family. Among these, poly(α-hydroxy acids) such as poly(glycolic acid), poly(lactic acid) and a range of their copolymers have historically comprised the bulk of published material on biodegradable polyesters and have a long history of use as synthetic biodegradable materials in a number of clinical applications. Poly(glycolic acid), poly(lactic acid) and their copolymers, poly-p-dioxanone, and copolymers of trimethylene carbonate and glycolide have been the most widely used as scaffolds. Their major applications include as resorbable sutures, drug delivery systems and orthopaedic fixation devices such as pins, rods and screws. Among the families of synthetic polymers, the polyesters have been attractive for these applications because of (i) their ease of degradation by hydrolysis of the ester linkage, (ii) degradation products are resorbed through the metabolic pathways in some cases and (iii) the potential to tailor the structure to alter degradation rates.

The recent interest in finding tissue-engineered solutions to repair damaged tissues and organs due to injury/disease has led to the development of new degradable polymers that meet a number of demanding requirements. These requirements range from the ability of the polymer scaffold to provide mechanical support during tissue growth and gradual degradation to biocompatible products, to more demanding requirements such as the ability to incorporate drugs, cells and growth factors, for example, and provide cell-conductive and inductive environments as well as promotion of the healing process. Drugs to suppress inflammatory response and promote the healing process can be incorporated within the biodegradable polymer scaffold or as a drug-eluting coating on the surface of the scaffold. Many of the currently available degradable polymers do not meet all of the requirements to be used in such applications. Most biodegradable polymers in the polyester and ester family, for example, are hydrophobic in nature and as such, only a limited number of drugs can be incorporated into such polymers.

In particular, biodegradable synthetic polymers with appropriate mechanical properties are sought after for the development of biodegradable stents and stent coatings for the treatment of coronary artery disease by percutaneous intervention. Stents provide mechanical support for the vessel and keep the lumen open to its normal diameter while tissue growth takes place to repair the affected vessel wall. Current stents are fabricated using metals such as stainless steel or nickel-titanium alloys, and once deployed these stents remain permanently within the vessel. Biodegradable polymers have the advantage of being removable from the vessel through polymer degradation and resorption once the vessel is repaired. This leaves the repaired vessel free of foreign material and allows re-stenting if needed in the future. Biodegradable polymers can also be useful in delivering drugs such as sirolimus, everolimus and paclitaxel D-actinomycin, all of which help to inhibit the formation of neointimal hyperplasia by suppression of platelet activation, suppression of inflammatory response, and promotion of the healing.

Scaffolds made from synthetic and natural polymers, and ceramics have been investigated extensively for orthopaedic repair. The use of scaffolds has advantages such as the ability to generate desired pore structures and the ability to match size, shape and mechanical properties to suit a variety of applications. However, shaping these scaffolds to fit cavities or defects with complicated geometries, to bond to bone tissue, and to incorporate cells, drugs and growth factors, and the requirements of open surgery are a few major disadvantages of the use of known scaffold materials.

The most common synthetic polymers used in fabricating scaffolds for growing cells and for biodegradable stents and stent coatings belong to the polyester family. For example, poly(glycolic acid) and poly(lactic acid) have been the most commonly used polymers because of their relative ease of degradation under hydrolytic conditions and the resorption of the degradation products into the body. However, these polymers have a number of disadvantages, including rapid loss of mechanical properties, long degradation times, difficulty in processing, and the acidity of degradation products resulting in tissue necrosis. These polymers, when used in biodegradable stents, have to be heated during the deployment process to temperatures as high as 70° C. which can cause cell damage.

Common methods that are currently employed for the synthesis of three dimensional biodegradable tissue engineering scaffolds include: porogen leaching, gas foaming, phase separation and the use of non-woven mesh. All of these methods have disadvantages including that:
- they require a mould to shape the scaffold—this is costly and can only produce a single shape;
- these methods offer little or no control over the orientation of the pores and degree of interconnectivity;
- usually a polymer skin forms on a moulded scaffold (even if it is porous) which can require extensive post-synthesis treatment; and
- some of the methods of scaffold fabrication such as phase separation and porogen leaching often involve the use of toxic organic solvents which is undesirable.

A controlled rapid prototyping method can address these problems. The shape of the mould can be quickly altered by computer design, the direction and degree of porosity can be specified to exact levels, a polymer skin is not formed in production, and the process is solvent free. When fabricating scaffolds such as stents for example, the process can be modified to deposit a grid like layout with polymer strands to dimensions and patterns specific to the stent design. The grid structure can then be used to fabricate the stent. Alternatively, the grid structure could be deposited on a rotating mandrel to fabricate the stent in one operation.

There are a number of different rapid prototyping machines available in the marketplace.

Synthetic polymers that can be used in such rapid prototyping apparatus need to meet specific property requirements which include melt processing characteristics, mechanical properties and other properties. For example, in fused deposition modelling (FDM) applications, the polymer must be able to be melt-processed into a filament of appropriate diameter for the rate of extrusion of the particular FDM apparatus.

Most synthetic biodegradable polymers do not meet the requisite property requirements. A review of the literature indicates that among the biodegradable polymers only poly-(ϵ-caprolactone) meets some of the requirements. Hutmacher et al at the National University of Singapore (Biomaterials, 24: 4445-4448, 2003) have reported the use of poly-(ϵ-caprolactone) (PCL) (MW 80,000) to fabricate tissue engineering scaffolds. They have also reported the use of hydroxyapatite as a filler (Schantz et al, Materials Science and Engineering 20: 9-17, 2002) in PCL to fabricate 3D constructs for bone tissue applications. A report by a group from the University of Nottingham (Christian et al, Composites: Part A, 32: 969-976, 2001), discusses PCL impregnated with long glass fibre in a MDM (Material Deposition Modelling) process to fabricate scaffolds. Commercially the market for biodegradable structures with interconnected pores is very large and growing rapidly. One product available is Degrapol® foam which is based on polyurethanes but they have much less control of the degree of porosity, orientation of pores and pore morphology, and it is available only as small foam discs (except on special order).

Polymers that can be used to fabricate biodegradable scaffolds using rapid prototyping techniques such as FDM need to meet a set of criteria including that:
- the polymer must be thermoplastic;
- the polymer must be extrudable;
- the filament must be mechanically stiff and have a low melt viscosity (a high Melt Flow Index); and
- the polymer must be biodegradable and biocompatible (eg. contain groups that are liable to hydrolyse and have degradation products that are non-toxic).

In short, the use of rapid prototyping machines to make porous, highly controlled and interconnected tissue engineering structures requires a complex combination of various techniques including polymer chemistry, polymer processing, rapid prototyping and tissue engineering and, accordingly, is particularly complex.

Accordingly, there is a need for biocompatible and biodegradable polymers that can be processed using methods including rapid prototyping as well as thermal and solvent based methods to fabricate scaffolds and coatings for various biomedical applications including tissue engineering.

It is thus one object of this invention to develop polymers with properties suited to use in rapid prototyping techniques which will, in turn, enable the fabrication of three dimensional scaffolds with complicated structures for use in tissue growth and repair therapies and technologies, including the fabrication of stents, and coatings for stents useful in drug delivery.

SUMMARY OF THE INVENTION

To this end, there is provided a biocompatible biodegradable polyurethane or polyurethane/urea comprising isocyanates, polyol and a conventional chain extender and/or a chain extender having a hydrolysable linking group. Preferably the isocyanates are diisocyanates. The polyurethane or polyurethane/urea may also be prepared using only a diisocyanate and a chain extender wherein the chain extender in this instance has dual functionality both as a conventional chain extender and as a polyol. Preferably the polyurethanes or polyurethane/ureas are thermoplastic.

Preferably the biocompatible, biodegradable polyurethanes or polyurethane/ureas of the invention are of the general formula

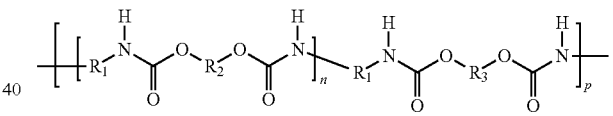

where $R_1$ is from the isocyanate, $R_2$ is from the chain extender and $R_3$ is from the soft segment polyol. The pronumeral 'n' represents the average number of repeat units in the hard segment. The pronumeral 'p' is proportional to the molecular weight of the polymer and includes both the hard segment repeat units and the soft segment.

Throughout this specification, the term "polyol" should be taken to mean a molecule which has at least two or more functional hydroxyl groups that can react with isocyanate groups to form urethane groups. Examples of polyols include but are not limited to diols, triols, and polyols such as macrodiols. Preferably the polyol has a molecular weight of 200-1000, more preferably 200-600, and even more preferably 200-400. The polyol may be terminated by, for example, a hydroxyl, thiol or carboxylic acid group.

Isocyanates suitable for preparation of the polyurethanes or polyurethane/ureas of the invention are those which are selected from the group consisting of optionally substituted aliphatic, aromatic and hindered isocyanates.

Throughout this specification, the term "chain extender" should be taken to mean a low molecular weight compound having two or more functional groups that are reactive towards isocyanate and having a molecular weight of less than 350. Chain extenders include functional monomers with degradable arms. The chain extender may be employed to introduce easily degradable hard segment components into the polyurethane or polyurethane/urea structure. Incorporating such chain extenders allows preparation of easily degradable polyurethanes with fewer degradation products. For example, polyurethane based on ethyl-lysine diisocyanate and glycolic acid based polyol and chain extender degrades to bioresorbable glycolic acid, lysine, ethylene glycol and ethanol.

"Degradable arms" according to the invention are any molecular moiety which may be part of the chain extenders and the molecular moiety structure is preferably biocompatible and bioresorbable on in vivo degradation of the biocompatible, biodegradable polyurethanes or polyurethane/ureas.

A "hard segment" polymer according to the invention is one which imbues the copolymer with its physical strength which arises from the nature of the chain extender and the isocyanate selected.

According to a preferred embodiment of the invention, the hard segment represents 20 to 100% by weight of the polyurethane or polyurethane/urea. Where the hard segment represents 100% by weight, the chain extender has a dual functionality of being both a conventional chain extender and a polyol.

Throughout this specification the term "comprises/comprising" when used is taken to specify the presence of stated features, integers, steps or components but does not preclude the presence or addition of one or more other features, integers, steps, components or groups thereof.

It has been found that the polyurethanes and polyurethane/ureas according to the invention form porous or non-porous cross-linked or linear polymers which can be used as tissue engineering scaffolds, and may be used in rapid prototyping techniques including FDM. It has also been found that certain of the biodegradable polyurethanes according to the invention exhibit a glass transition between room temperature and 37° C. This property can be used to extrude hard materials on FDM apparatus (going in at 20° C.) which will soften and even become elastomeric in vivo or while growing cells on scaffolds in a bioreactor at physiological temperatures of 37° C. This is also a very useful property for soft tissue applications.

The polyurethanes and polyurethane/ureas can be sterilized without risk to their physical and chemical characteristics, preferably using gamma radiation to ensure sterility.

The polyurethanes and polyurethane/ureas may incorporate biological and inorganic components selected for their ability to aid tissue repair in vivo, or to create certain physical characteristics for rapid prototyping purposes. When cured, the polyurethanes and polyurethane/ureas according to the invention form a biodegradable biocompatible scaffold which may be porous and contain interpenetrating polymer networks so as to enable the inclusion of biological and inorganic components. These biological and inorganic components which are preferably selected from the group consisting of cells, progenitor cells, growth factors, other components for supporting cell growth, drugs, calcium phosphate, hydroxyapatite, hyaluronic acid, nanoparticulate tricalcium phosphate and hydroxyapatite type fillers, adhesives including fibrin, collagen and transglutaminase systems, surfactants including siloxane surfactants, silica particles, powdered silica, hollow fibres which may be used to seed cells in the polyurethanes, and other porogens including, for example, gelatin beads. The biological and inorganic components may be present in quantities according to need, especially in the case of the living additives such as cells and progenitor cells. Amounts of up to at least 20% w/w may be acceptable.

The invention also provides a biodegradable, biocompatible polymeric scaffold comprising a cured biocompatible, biodegradable polyurethane or polyurethane/urea being the reaction product of isocyanate, polyol and a conventional chain extender and/or a chain extender having a hydrolysable linking group.

In the biodegradable, biocompatible polymeric scaffolds according to this aspect of the invention the isocyanates are preferably diisocyanates. The scaffolds may also be prepared using a diisocyanate and a chain extender wherein the chain extender has the dual functionality of a conventional chain extender and a polyol. Preferably the isocyanate is selected from the group consisting of optionally substituted aliphatic, aromatic and hindered isocyanates.

The scaffolds may preferably incorporate biological and inorganic components which are desirably selected from the group consisting of cells, progenitor cells, growth factors, other components for supporting cell growth, drugs, calcium phosphate, hydroxyapatite, hyaluronic acid, nanoparticulate tricalcium phosphate and hydroxyapatite type fillers, adhesives including fibrin, collagen and transglutaminase systems, surfactants including siloxane surfactants, silica particles, powdered silica, hollow fibres which may be used to seed cells in the polyurethanes, and other porogens including, for example, gelatin beads. The biological and inorganic components may be present in quantities according to need, especially in the case of the living additives such as cells and progenitor cells. Amounts of up to at least 20% w/w may be acceptable.

Preferably the cured scaffolds according to this aspect of the invention have a compressive strength in the range of 0.05-100 MPa. The compressive strength of the scaffold will vary according to its porosity and according to the biological components added. Preferably the scaffolds have pores in the size range of 100-500 micron, more preferably 150-300 micron.

More preferably the porous scaffolds are seeded with living biological components or drugs selected so as to aid the tissue repair process in the patient being treated. The biological components so selected may be cells, progenitor cells, growth factors and other components for supporting cell growth. Suitable cells may include osteoblasts, chondrocytes, fibroblasts or other precursor cells. Suitable drugs are any which assist in the tissue engineering application of interest.

In one preferred embodiment of the invention, the scaffold is a biodegradable stent useful in treatment of coronary heart disease.

In another aspect of the invention, the biodegradable biocompatible polyurethanes or polyurethane/ureas of the invention are utilized as stent coatings in the treatment of coronary heart disease.

In another aspect of the invention, there is provided a use of polyurethanes and polyurethane/ureas according to the invention in rapid prototyping techniques such as fused deposition modeling.

In another aspect of the invention, there is provided a use of polyurethanes and polyurethane/ureas according to the invention in tissue repair or engineering in a patient requiring such treatment the use comprising inserting in said patient a scaffold which is the cured end product of said biocompatible, biodegradable polyurethane or polyurethane/urea according to the invention prepared by rapid prototyping techniques such as, but not limited to, fused deposition modelling. The polyurethane or polyurethane/urea may preferably include additives or drugs to assist for example in the repair of the damaged bone or cartilage such as cells, progenitor cells, growth factors, or other suitable materials or other additives, such as pharmaceuticals for use in drug delivery. Biological additives used may preferably include osteoblasts, chondrocytes, fibroblasts, fibrin, collagen, transglutaminase systems and the like.

The invention also provides for the use of biocompatible, biodegradable polyurethanes and polyurethane/ureas according to the invention as a tissue engineering scaffold for assistance in tissue engineering applications such as bone and cartilage repair.

Other embodiments of the invention will be evident from the following detailed description of various aspects of the invention.

DETAILED DESCRIPTION OF THE INVENTION

Figure 1:
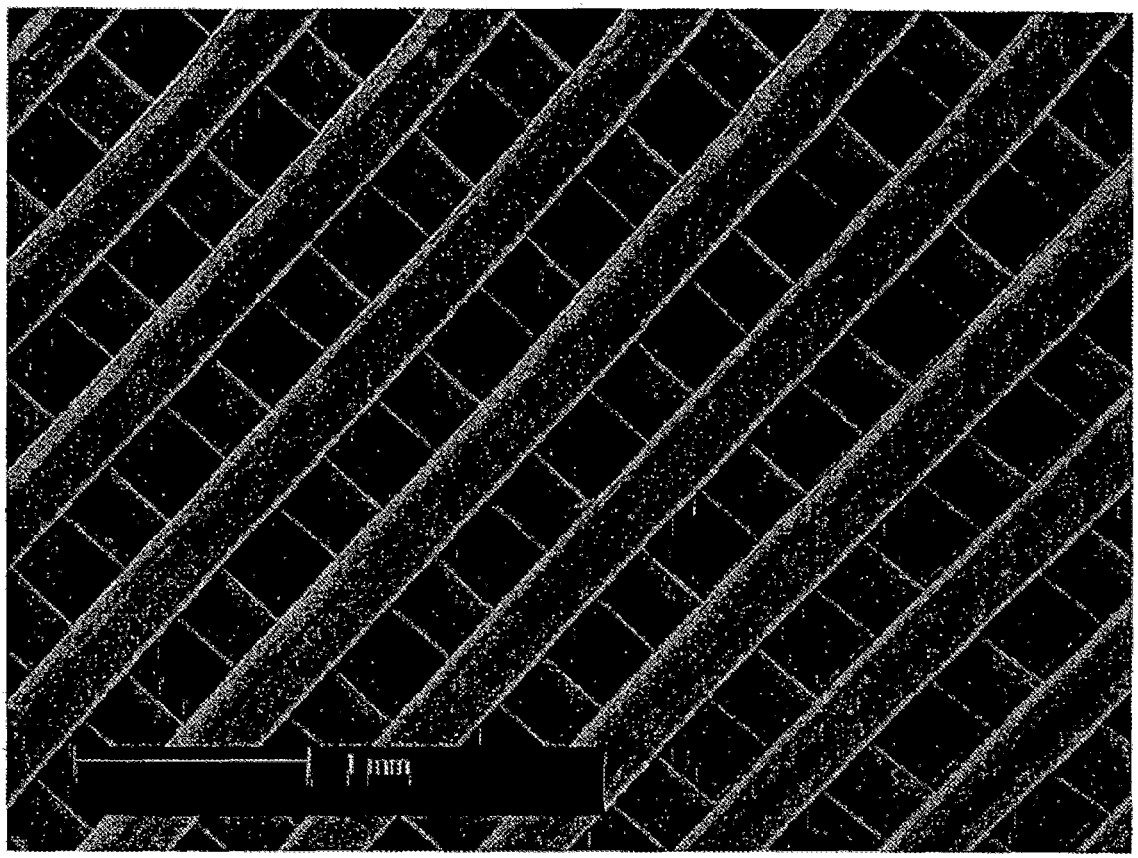
FIG. 1 shows the SEM of a polyurethane scaffold made according to Example 1.

The present invention provides polyurethanes and polyurethane/ureas which are particularly suited to rapid prototyping techniques such as fused deposition modelling and therefore have specific characteristics as described in the preamble of this specification.

In a preferred form, this invention provides a biocompatible biodegradable polyurethane or polyurethane/urea comprising diisocyanates, polyol of molecular weight 200-600 and a conventional chain extender and/or a chain extender having a hydrolysable linking group.

Isocyanates suitable for preparing polyurethanes and polyurethane/ureas according to the invention include but are not limited to the following:

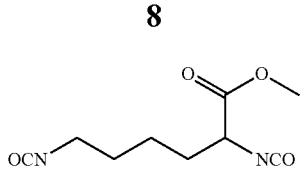

MLDI—lysine diisocyanate methyl ester

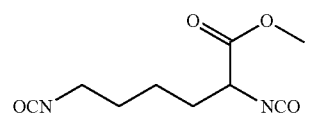

ELDI—lysine diisocyanate ethyl ester

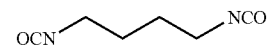

BDI—Butane diisocyanate

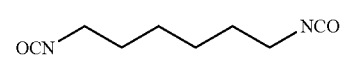

HDI—hexamethylene diisocyanate

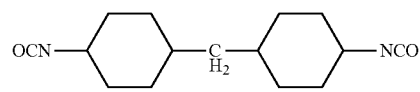

$H_{12}MDI$—4,4'-methylene-bis(cyclohexyl isocyanate)

Polyols or "soft segments" which may be used to prepare the polyurethanes and polyurethane/ureas of the invention are most preferably those having a molecular weight of 200-400. The structure of the polyol in the present invention is preferably:

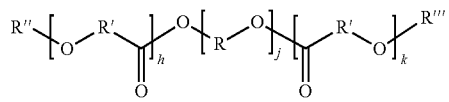

where h and/or k can equal 0 (as is the case of the dimer, eg, h=0, j=1 and k=1) or are integers as is j and R'' and R''' independently of each other are hydrogen, hydroxy alkyl, aminoalkyl (both primary and secondary) or carboxy alkyl and R and R' cannot be hydrogen, but can be a linear or branched alkyl, alkenyl, aminoalkyl, alkoxy or aryl. The molecular weight of the entire structure is more preferably 120 to 400. Less preferably the molecular weight can be up to 2000 and much less preferably above 2000. Four examples of suitable soft segments are as follows:

Poly(ε-caprolactone) diol, MW 400 (from Example 1): where R is $(CH_2-CH_2)$, R' is $(CH_2)_5$, R" and R''' are both H, and j=1 and (h+k)=2.96

(Glycolic acid-ethylene glycol) dimer (from Example 8): where R is $(CH_2-CH_2)$, R' is $(CH_2)$, R" and R''' are both H, j=1 and (h+k)=1

Poly(ethylene glycol), MW 400 (from Example 4): h=0, k=0, j=~13, R is $(CH_2-CH_2)$, and R" and R''' are both H Poly(ethylene glycol)bis(3-aminopropyl) terminated (Aldrich): where R is (CH$_2$—CH$_2$), R'' and R''' are both —(CH$_2$)$_3$NH$_2$, j=34 and (h+k)=0

Either or both of R and R' can contain nonlinear structures, for example where R'=(CH$_2$CHCH$_3$) which is lactic acid. However, the R and R' should preferably not contain groups such as OH and NH$_2$ which are likely to cause crosslinking. Suitable compounds include but are not limited to the following polyester polyols:

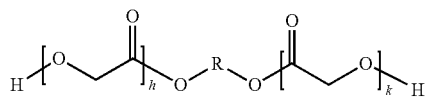

PGA—Poly-(glycolic acid) diol, where R is typically —(CH$_2$CH$_2$)—

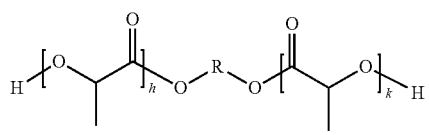

PLA—Poly-(lactic acid) diol, where R is typically —(CH$_2$CH$_2$)—

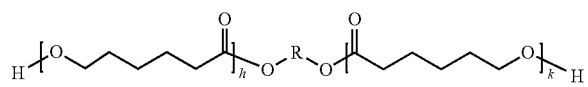

PCL—Poly-(ε-caprolactone) diol, where R is typically —(CH$_2$CH$_2$)—

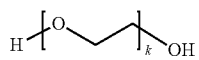

PEG—Poly-(ethylene glycol)

Examples of other polyols which may act as soft segments include poly-(4-hydroxybutyrate) diol (P4HB diol), poly-(3-hydroxybutyrate) diol (P3HB diol), polypropylene glycol and any copolymers of the aforesaid including PLGA diol, P(LA/CL) diol, P(3HB/4HB) diol.

Chain extenders according to the invention are any low molecular weight molecule having two or more functional groups which when reacted with diisocyanates form a urethane or urea linkage. Preferably the chain extender is difunctional and examples of such chain extenders are diols, dithiols, diamines, amino alcohols and dicarboxylic acids. Diols are also relatively non-toxic and can be resorbed or excreted from the body upon degradation and examples include ethylene glycol, diethylene glycol, tetraethylene glycol, 1,3-propane diol, 1,4-butane diol, 1,6-hexane diol, GA-EG dimer, LA-EG dimer, trimers including a combination of LA and/or GA and EG, and oligomeric diols such as dimers and trimers. Examples of amines that may be used are butane diamine, ethanolamine, glycine and lysine. Incorporated into the hard segment, these chain extenders increase degradation. Esters in the hard segment degrade much faster than urethane linkages. The following chain extenders are illustrated:

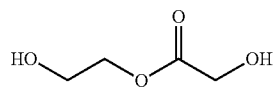

A degradable diol chain extender EG-GA diol, MW~120

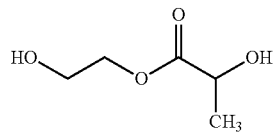

A degradable chain extender EG-LA diol, MW~134

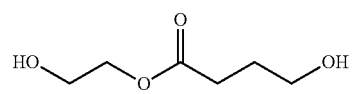

A degradable diol chain extender EG-4HB diol, MW~148

Preferred polyurethane and polyurethane/ureas prepared according to the invention may utilise PCL diol, PGA diol, PLA diol or PEG diol and HDI/EG as the hard segment. Another preferred polyurethane or polyurethane/urea according to the invention includes a diol of poly(4-hydroxybutyrate) or copolymers therewith to give an improved range of properties and degradation rates.

According to the present invention, the monomeric units of the polyurethanes or polyurethane/ureas of the invention are preferably reacted by bulk polymerisation to form a straight-chain poly-(ester-urethane) block copolymer. Catalysts such as titanium butoxide, Tyzor-LA, stannous octoate, ferric acetyl acetonate, magnesium methoxide, zinc octoate, manganese 2-ethyl hexanoate, amine catalyst may, if desired, be used in such polymerisation. The general form of the repeat units in the polymer after polymerisation is:

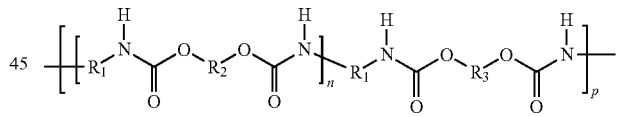

Where R$_1$ is from the diisocyanate e.g. hexamethylene diisocyanate. R$_2$ is from a low molecular weight diol chain extender e.g. ethylene glycol. R$_3$ is from a soft segment diol e.g. PCL diol (MW 400). The pronumeral 'n' represents the average number of repeat units in the hard segment. The pronumeral 'p' is proportional to the molecular weight of the polymer and includes both the hard segment repeat units and the soft segment.

In a preferred embodiment of the invention, the hard segment represents 20 to 100% by weight of the polyurethane/polyurethane/urea. More preferably the hard segment represents 60 to 70% by weight. The polyol and chain extender may be the same compound and this corresponds to the embodiment where the hard segment corresponds to 100% by weight of the polyurethane/polyurethane/urea. It has been found that there must be a reasonably high proportion of hard segment for the materials to have adequate properties to extrude through FDM as well as a reasonably high melt flow index.

EXAMPLES

The following examples are not intended to limit the invention but rather illustrate the nature of the broad invention and its applicability.

Example 1

Preparation of 12TM4 (65% Hard Segment, 35% PCL Diol 400)

Materials: The PCL diol (molecular weight 402.1) from ERA Polymer Pty was dried at 90° C. for 4 hours under vacuum (0.1 torr). Ethylene glycol (Aldrich) was degassed at 90° C. under vacuum (0.1 torr) for three hours and HDI (Aldrich) was used as received. A polyurethane composition based on a mixture of PCL diol, EG and HDI was prepared by a one-step bulk polymerisation procedure. Stannous octoate (Aldrich) was kept moisture-free and used as received.

A mixture of PCL (25.000 g) and EG (9.696 g) and stannous octoate (0.0714 g) was placed in a 100 ml predried polypropylene beaker, covered with aluminium foil and heated to 70° C. under nitrogen in a laboratory oven. HDI (36.732 g) was weighed in a separate wet-tared predried polypropylene beaker and added to the PCUEG/stannous octoate beaker and stirred manually until gelation occurred (90 seconds), at which time the viscous mixture was poured onto a Teflon coated metal tray to cure at 100° C. for a period of about 18 hours. The resulting polymer was clear, colourless and tough.

A sample of the polymer after curing was compression moulded at 175° C. to a 1 mm thick flat sheet for tensile testing. Dumbbells punched from the sheet were tensile tested using an Instron Model 5568 Universal Testing Machine.

The mechanical properties of the materials prepared in EXAMPLE 1 were examined and the results are shown in Table 1.

Example 1a

Post-Synthesis Processing

The solid polymer sheet was chopped into about 1 cm$^3$ pieces with clean tin-snips, cooled in liquid nitrogen and ground into a powder using a cryogrinder. The polymer powder was then dried at 100° C. under vacuum overnight. The polymer was extruded on a mini-extruder equipped with a 1.7 mm die at 180° C. and 40 rpm. The polymer was taken off by a belt conveyor and cooled at ambient temperature in air without water bath. The filament was spooled and kept under nitrogen in a moisture-free environment for at least one week prior to use.

The polymer filament was fed though the FDM apparatus and a small lattice was made to show that the material was suitable for FDM. The scaffolds were characterised by light microscopy and SEM and were shown to have very good precision and weld. It has been shown to work with a number of commercially available nozzle diameters.

The operating envelope temperature inside the machine was 25° C. and the heating zone was set at 168° C. SEM micrographs and optical microscopy of FDM scaffolds are shown in FIGS. 1-6.

Example 2

Preparation of 12TM1 (a Softer Material than Example 1, 60% Hard Segment, 40% PCL Diol 400)

Materials: The PCL diol (molecular weight 402.1) from ERA Polymer Pty was dried at 90° C. for 4 hours under vacuum (0.1 torr). Ethylene glycol (Aldrich) was degassed at 90° C./0.1 torr for 3 hours and HDI (Aldrich) was used as received. A polyurethane composition based on a mixture of PCL diol, EG and HDI was prepared by a one-step bulk polymerisation procedure. Stannous octoate (Aldrich) was kept moisture-free and used as received.

A mixture of PCL (40.0 g) and EG (11.663 g) and stannous octoate (0.100 g) was placed in a 100 ml predried polypropylene beaker, covered with aluminium foil and heated to 70° C. under nitrogen in a laboratory oven. HDI (48.337 g) was weighed in a separate wet-tared predried polypropylene beaker, covered and then added to the PCUEG/stannous octoate beaker and stirred manually until gelation occurred (90 seconds). The viscous mixture was poured onto a Teflon coated metal tray to cure at 70° C. for a period of about 18 hours. The resulting polymer was clear, colourless and tough.

A sample of the polymer after curing was compression moulded at 170° C. to a 1 mm thick flat sheet for tensile testing. Dumbbells punched from the sheet were tensile tested using an Instron Model 5568 Universal Testing Machine.

The mechanical properties of the materials prepared in EXAMPLE 2 were examined and the results are shown in Table 1.

Example 2a

Post-Synthesis Processing

The solid polymer sheet was chopped into about 1 cm$^3$ pieces with clean tin-snips, cooled in liquid nitrogen and ground into powder using a cryogrinder. The polymer powder was then dried at 70° C. under vacuum overnight. The polymer was extruded on the mini-extruder equipped with a 1.7 mm die at 175° C. and 35-40 rpm. The polymer was taken off on a rotating shaft and cooled at ambient temperature in air without water bath. The filament was spooled and kept under nitrogen in a moisture-free environment for at least one week prior to use.

The polymer filament was fed though the FDM apparatus and a small lattice was made to show that the material was suitable for FDM.

Example 3

Preparation of 12TM6 (a Harder Material than Example 1, 70% Hard Segment, 30% PCL Diol 400)

Materials: The PCL diol (molecular weight 402.1) from ERA Polymer Pty was dried at 90° C. for 4 hours under vacuum (0.1 torr). Ethylene glycol (Aldrich) was degassed at 90° C./0.1 torr for 3 hours and HDL (Aldrich) was used as received. A polyurethane composition based on a mixture of PCL diol, EG and HDI was prepared by a one-step bulk polymerisation procedure. Stannous octoate (Aldrich) was kept moisture-free and used as received.

A mixture of PCL (21.0 g) and EG (10.840 g) and stannous octoate (0.070 g) was placed in a 100 ml predried polypropylene beaker, covered with aluminium foil and heated to 70° C. under nitrogen in a laboratory oven. HDI (38.160 g) was weighed in a separate predried polypropylene beaker and added to the PCL/EG/stannous octoate beaker and stirred until gelation occurred (60 seconds), at which time the viscous mixture was poured onto a Teflon coated metal tray to cure at 100° C. for a period of about 18 hours. The resulting polymer was clear, colourless and tough.

A sample of the polymer after curing was compression moulded at 175° C. to a 1 mm thick flat sheet for tensile testing. Dumbbells punched from the sheet were tensile tested using an Instron Model 5568 Universal Testing Machine.

The mechanical properties of the materials prepared in EXAMPLE 3 were examined and the results are shown in Table 1.

Example 3a

Post-Synthesis Processing

The solid polymer sheet was chopped into about 1 cm³ pieces with clean tin-snips, cooled in liquid nitrogen and ground into powder using a cryogrinder. The polymer powder was then dried at 70° C. under vacuum overnight. The polymer was extruded on the mini-extruder equipped with a 1.7 mm die at 175° C. and 40 rpm. The polymer was taken off on a rotating shaft and cooled at ambient temperature in air without water bath. The filament was spooled and kept under nitrogen in a moisture-free environment for at least one week prior to use.

The polymer filament was fed though the FDM apparatus and a small lattice was made to show that the material was suitable for FDM.

Example 4

Preparation of 14TM12 (Changing the Soft Segment to PEG Diol

Materials: The PEG diol (molecular weight 394.7) from Aldrich was dried at 90° C. for 4 hours under vacuum (0.1 torr). Ethylene glycol (Aldrich) was degassed at 90° C./0.1 torr for three hours and HDI (Aldrich) was used as received. A polyurethane composition based on a mixture of PCL diol, EG and HDI was prepared by a one-step bulk polymerisation procedure. Stannous octoate (Aldrich) was kept moisture-free and used as received.

A mixture of PEG (20.000 g) and EG (7.715 g) and stannous octoate (0.0571 g) was placed in a 100 ml predried polypropylene beaker, covered with aluminium foil and heated to 70° C. under nitrogen in a laboratory oven. HDI (29.428 g) was weighed in a separate predried polypropylene beaker, and added to the PEG/EG/stannous octoate beaker and stirred until gelation occurred (150 seconds), when the viscous mixture was poured onto a Teflon coated metal tray to cure at 70° C. for a period of about 18 hours. The resulting polymer was clear, colourless and tough.

A sample of the polymer after curing was compression moulded at 150° C. to a 1 mm thick flat sheet for tensile testing. Dumbbells punched from the sheet were tensile tested using an Instron Model 4032 Universal Testing Machine.

Example 4a

Post-Synthesis Processing

The solid polymer sheet was chopped into about 1 cm³ pieces with clean tin-snips, cooled in liquid nitrogen and ground into powder using a cryogrinder. The polymer powder was then dried at 100° C. under vacuum overnight. The polymer was extruded on the mini-extruder equipped with a 1.7 mm die at 150° C. and 40 rpm. The polymer was taken off by a belt conveyor and cooled at ambient temperature in air without water bath. The filament was spooled and kept under nitrogen in a moisture-free environment for at least one week prior to use.

The polymer filament was fed though the FDM apparatus and a small lattice was made to show that the material was suitable for FDM. The scaffolds were characterised by light microscopy and SEM and were shown to have very good precision and weld. It has been shown to work with a number of commercially available nozzle diameters.

The operating envelope temperature inside the machine was 25° C. and the heating zone was set at 168° C.

Example 5

Preparation of 14TM3-1 (Using a Different Diisocyanate—MLDI)

Materials: The PEG diol (molecular weight 394.7) from Aldrich was dried at 90° C. for 4 hours under vacuum (0.1 torr). Ethylene glycol (Aldrich) was degassed at 90° C./0.1 torr for 3 hours. Methyl ester of Lysine diisocyanate MLDI (Kyowa Hakko Kogyo CO. Ltd) was used as received. A polyurethane composition based on a mixture of PCL diol, EG and HDI was prepared by a one-step bulk polymerisation procedure. Stannous octoate (Aldrich) was kept moisture-free and used as received.

A mixture of PEG (12.814 g) and EG (16.380 g) and stannous octoate (0.0992 g) was placed in a 100 ml predried polypropylene beaker, covered with aluminium foil and heated to 70° C. under nitrogen in a laboratory oven. MLDI (70.00 g) was measured in a separate predried polypropylene beaker and added to the beaker containing mixture of PEG/EG/stannous octoate and stirred until gelation occurred (~300 seconds), at which time the viscous mixture was poured onto a Teflon coated metal tray to cure at 70° C. for a period of about 18 hours. The resulting polymer was clear, slightly golden in colour and tough.

A sample of the polymer after curing was compression moulded at 175° C. to a 1 mm thick flat sheet for tensile testing.

Example 6

Preparation of 16TM9 (100% Hard Segment Using MLDI and EG)

Materials: The EG (Aldrich) was degassed at 90° C./0.1 torr for three hours. MLDI (Kyowa Hakko Kogyo CO. Ltd) was used as received. A polyurethane composition based on a 1 to 1 ratio of MLDI and EG was prepared by a one-step bulk polymerisation procedure. Stannous octoate (Aldrich) was kept moisture free and used as received.

EG (22.000 g) and stannous octoate (0.0972 g) were weighed into a 100 ml predried polypropylene beaker, covered with aluminium foil and heated to 70° C. under nitrogen in a laboratory oven. MLDI (75.214 g) was measured in a separate predried polypropylene beaker, covered with aluminium foil and also heated under nitrogen at 70° C. before being added to the EG/stannous octoate and stirred until gelation occurred (~700 sec), at which time the viscous mixture was poured onto a Teflon coated metal tray to cure at 70° C. overnight for a period of about 18 hours. The resulting polymer was clear, golden in colour, very hard and brittle.

Example 6a

Post-Synthesis Processing

The melt flow index of the material prepared was measured to be 136 g/10 min with a 2.16 kg load.

Example 7

Preparation of 12TM19 Illustrating Shape Memory Effects (100% Hard Segment Using MLD1 and 2-ethyl-1,3-hexanediol)

Materials: The 2-ethyl-1,3-hexanediol (Fluka) was degassed at 90° C./0.1 torr for 3 hours. MLDI (Kyowa Hakko Kogyo CO. Ltd) was used as received. A polyurethane composition based on a 1 to 1 ratio of MLDI and 2-ethyl-1,3-hexanediol was prepared by a one-step bulk polymerisation procedure. Stannous octoate (Aldrich) was kept moisture free and used as received.

2-ethyl-1,3-hexanediol (8.269 g) and stannous octoate (0.021 g) were weighed into a 100 ml predried polypropylene beaker, covered with aluminium foil and heated to 70° C. under nitrogen in a laboratory oven. MLDI (12.000 g) was measured in a separate predried polypropylene beaker, covered with aluminium foil and also heated under nitrogen at 70° C. before being added to the 2-ethyl-1,3-hexanediol/stannous octoate and stirred until gelation occurred (~30 min), at which time the viscous mixture was poured onto a Teflon coated metal tray to cure at 70° C. overnight for a period of about 18 hours. The resulting polymer was clear, golden in colour, very hard and brittle.

Example 7a

Post-Synthesis Processing

DSC was taken on a Mettler DSC 30 and showed the Tg to be ~30° C. When left at room temperature it was hard and brittle but it reversibly softened in the hand and became elastic.

Example 8

Preparation of a Hydrolysable Chain Extender (15TM7, GA-EG Diol)

22.19 g of glycolic acid (GA) (Sigma) was heated at 200° C. under nitrogen outgassing in a round bottomed flask equipped with a stillhead sidearm and condenser to collect the water runoff. After 18 hours the nitrogen was stopped and vacuum applied (0.1 torr), by which stage the GA had polymerised to a white solid (PGA). Dry ethylene glycol (EG) (Aldrich) (106 g) was added to the PGA in an approximate ratio of 5:1 in order to transesterify the polymer. This was refluxed for a period of 8 hours in total and was followed by GPC until there were three major products: EG, EG-GA and some EG-GA-GA. The EG was removed under vacuum and heat and the resulting chain extender was used to make a polyurethane (16TM7).

Example 8a

Preparation of a Polyurethane Using a Hydrolysable Chain Extender (16TM7 from Example 8)

Materials: The 15TM7 (GA-EG diol chain extender) was degassed at 90° C./0.1 torr for three hours, as was the PCL diol (MW400). HDI (Aldrich) was used as received. A polyurethane composition based on an 80% hard segment composition was prepared by a one-step bulk polymerisation procedure. Stannous octoate (Aldrich) was kept moisture free and used as received.

15TM7 (30.73 g) and PCL diol (MW402.099) (20.05 g) and stannous octoate (0.100 g) were weighed into a 100 ml predried polypropylene beaker, covered with aluminium foil and heated to 70° C. under nitrogen in. a laboratory oven. HDI (49.47 g) was measured in a separate predried polypropylene beaker, covered with aluminium foil and also heated under nitrogen at 70° C. before being added to the PCL diol/15TM7/stannous octoate mixture and stirred until gelation occurred when the viscous mixture was poured onto a Teflon coated metal tray to cure at 70° C. overnight for a period of about 18 hours. The resulting polymer was slightly cloudy, hard but flexible.

TABLE 1

Mechanical properties of some PCL-based polyurethanes with different hard segment percentages

| Code | Hard segment (Wt %) | Elong (%) | Y. Mod (MPa) | UTS (MPa) | Shore (D) |
|---|---|---|---|---|---|
| 12TM1 | 60 | 899 ± 189 | 103 ± 5 | 41 ± 1 | 44 |
| 12TM4 | 65 | 1300 ± 42 | 112 ± 3 | 54 ± 5 | 52 |
| 12TM6 | 70 | 1537 ± 141 | 143 ± 7 | 56 ± 6 | 57 |

TABLE 2

Melt flow index of various materials
The Melt Flow Index of various materials according to the present invention was calculated, along with the readily available commercial materials: acrylonitrile butadiene styrene (ABS), polyamide and investment casting wax (ICW). In order to be suitable for FDM, the materials of the present invention preferably should have a MFI which is similar or higher than that of the commercial samples, without significant degradation of the material.

| Material | Temperature (° C.) | MFI (g/10 min), 2.16 kg weight |
|---|---|---|
| ABS | 270 | 8.5 |
| Polyamide | 140 | 75 |
| ICW | 73 | 9.5 |
| 14TM3-1 | 160 | 7.64 |
| 12TM4-6 | 165 | 10.43 |
| 16TM9 | 160 | 136 |

It will be appreciated that the scope of the invention is not limited to the specific examples described herein but extends to the general inventive concepts defined. None of the examples should be considered limiting.

Example 9

Cell Compatibility of Scaffolds

This example illustrates the cell compatibility of scaffolds fabricated using polymers prepared according to the invention.

Polymers were prepared according to the procedure disclosed in Example 1 and 3D scaffolds were fabricated using the procedure described in EXAMPLE 1A.

Figure 2:
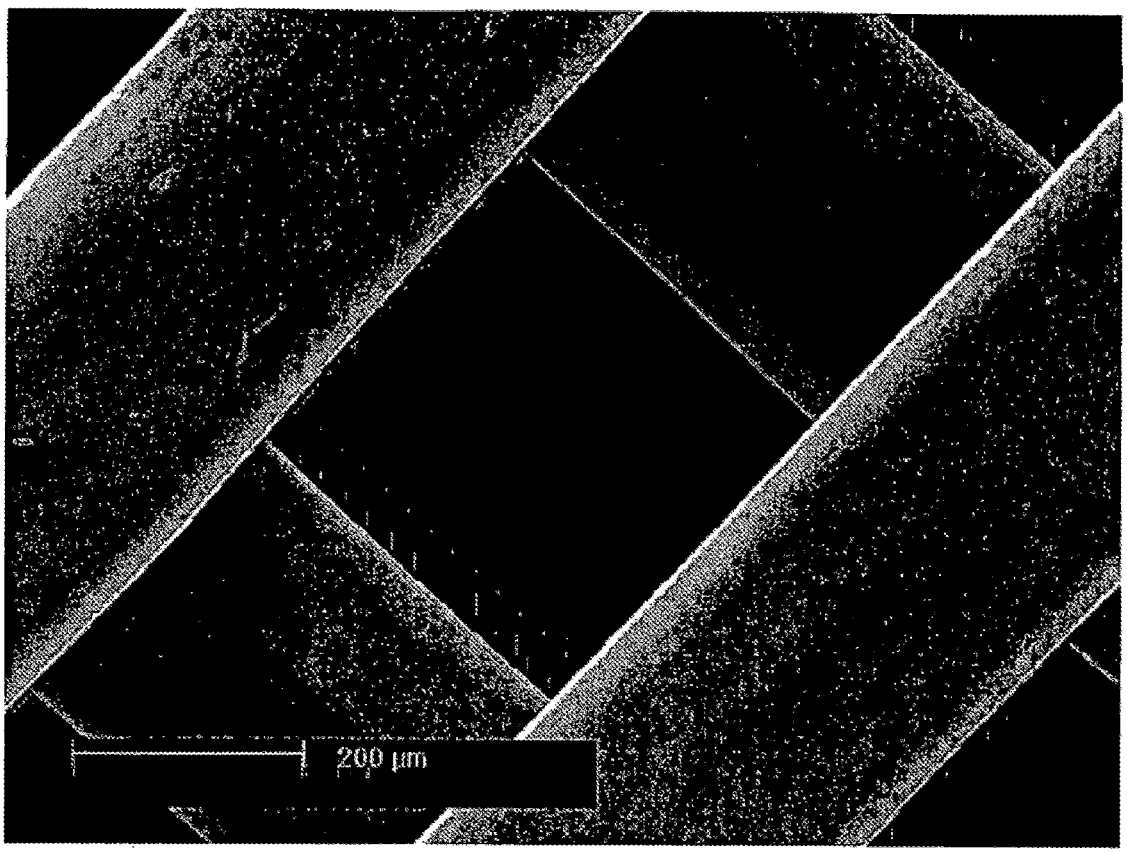
FIG. 2 shows the SEM of a polyurethane scaffold made according to Example 1 but under higher magnification.
Figure 3:
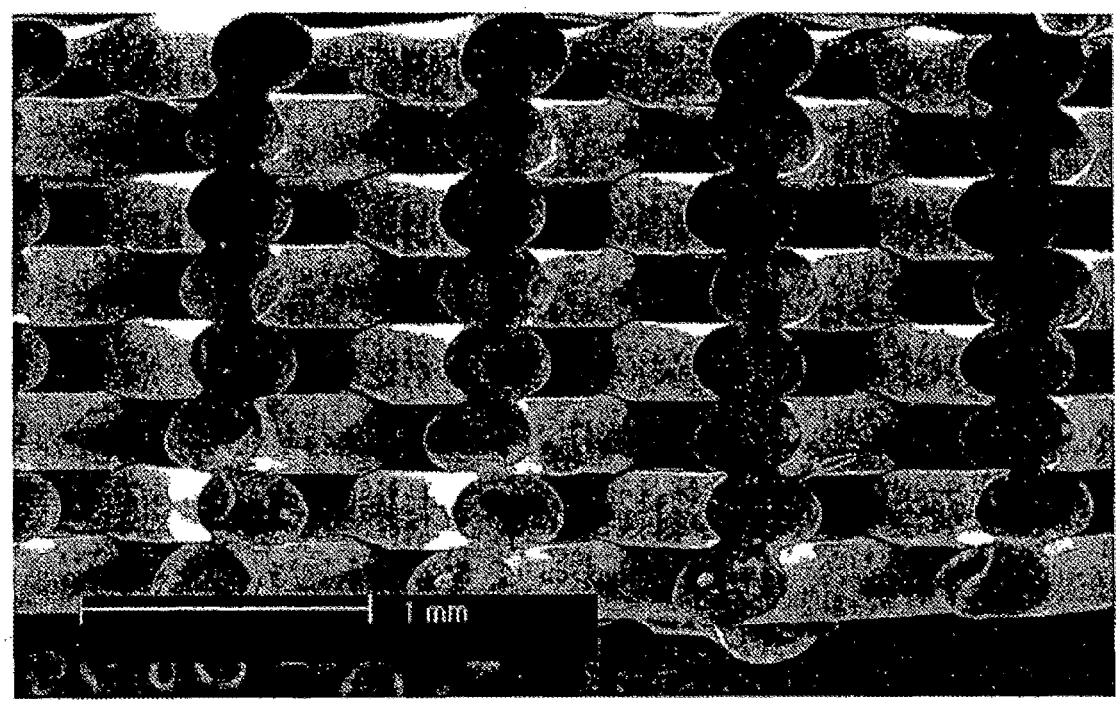
FIG. 3 shows the scaffold of Example 1 and demonstrates stratified design and overlap in the z axis.
Figure 4:
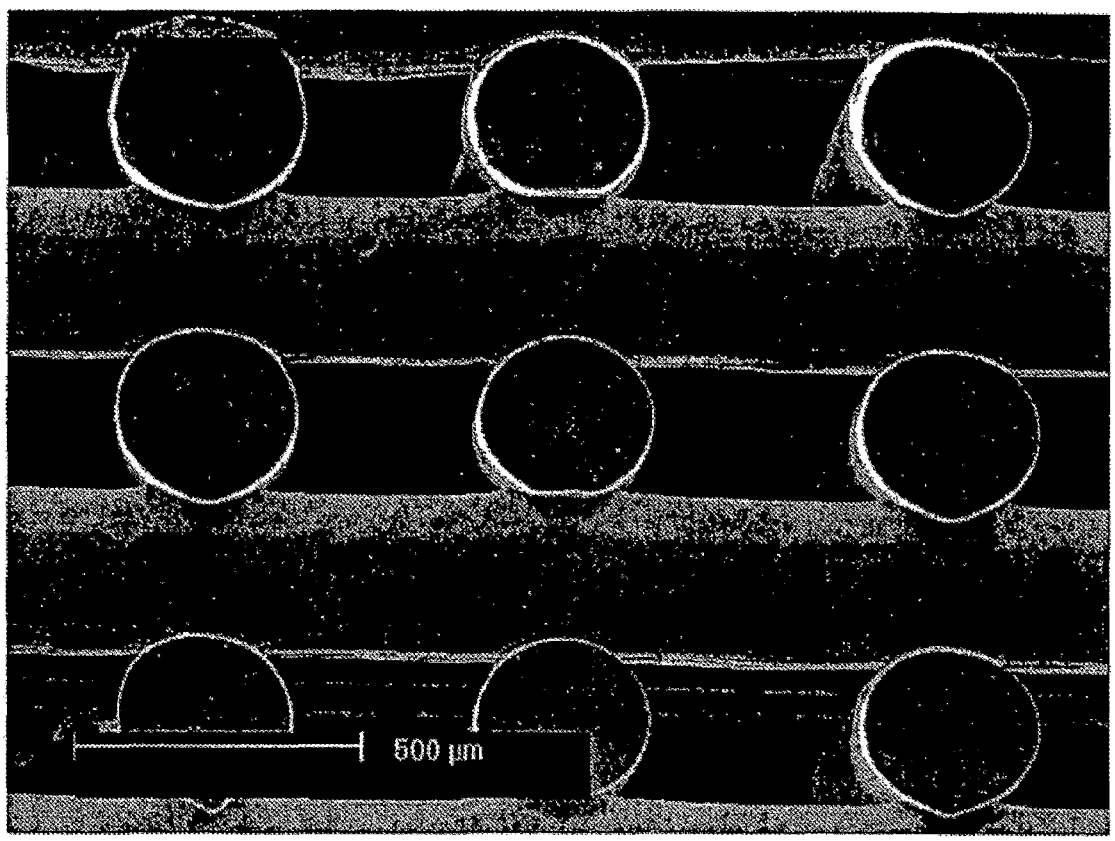
FIG. 4 shows the scaffold of Example 1 showing the interconnected pores in a regular section.
Figure 5:
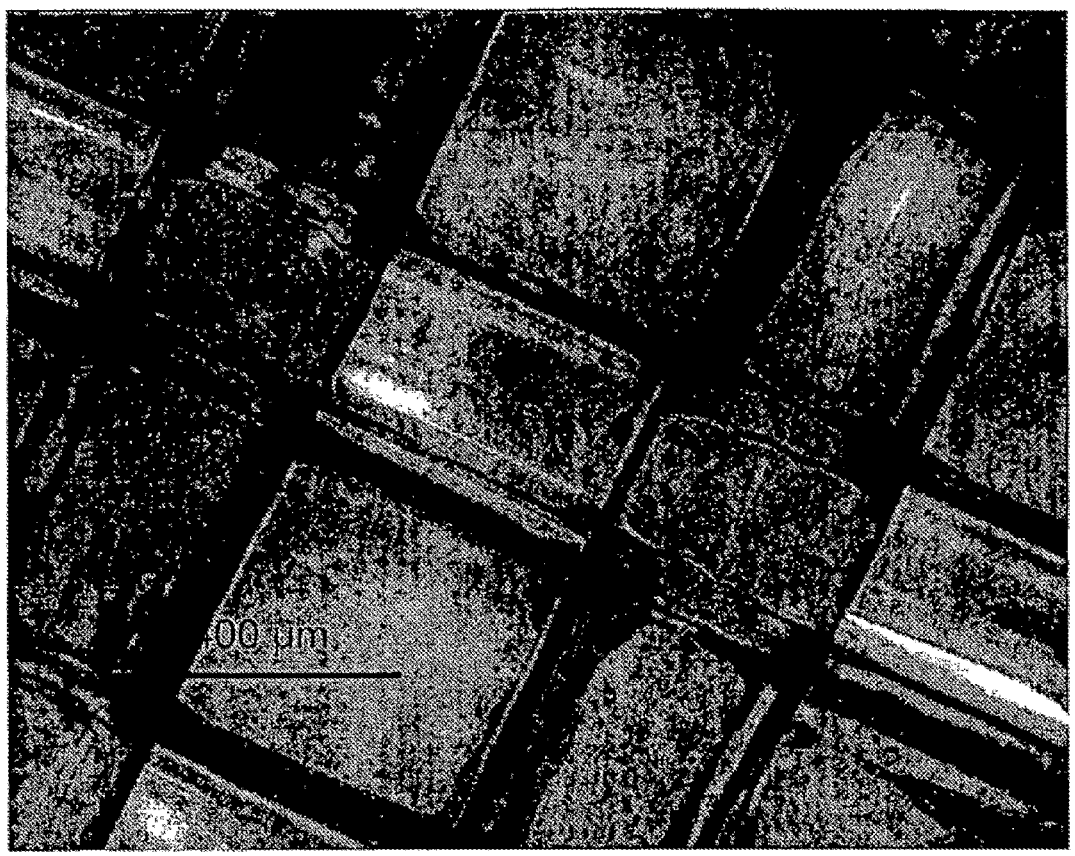
FIG. 5 shows the scaffold of Example 1 under light microscopy and demonstrates optical clarity and fusion.
Figure 6:
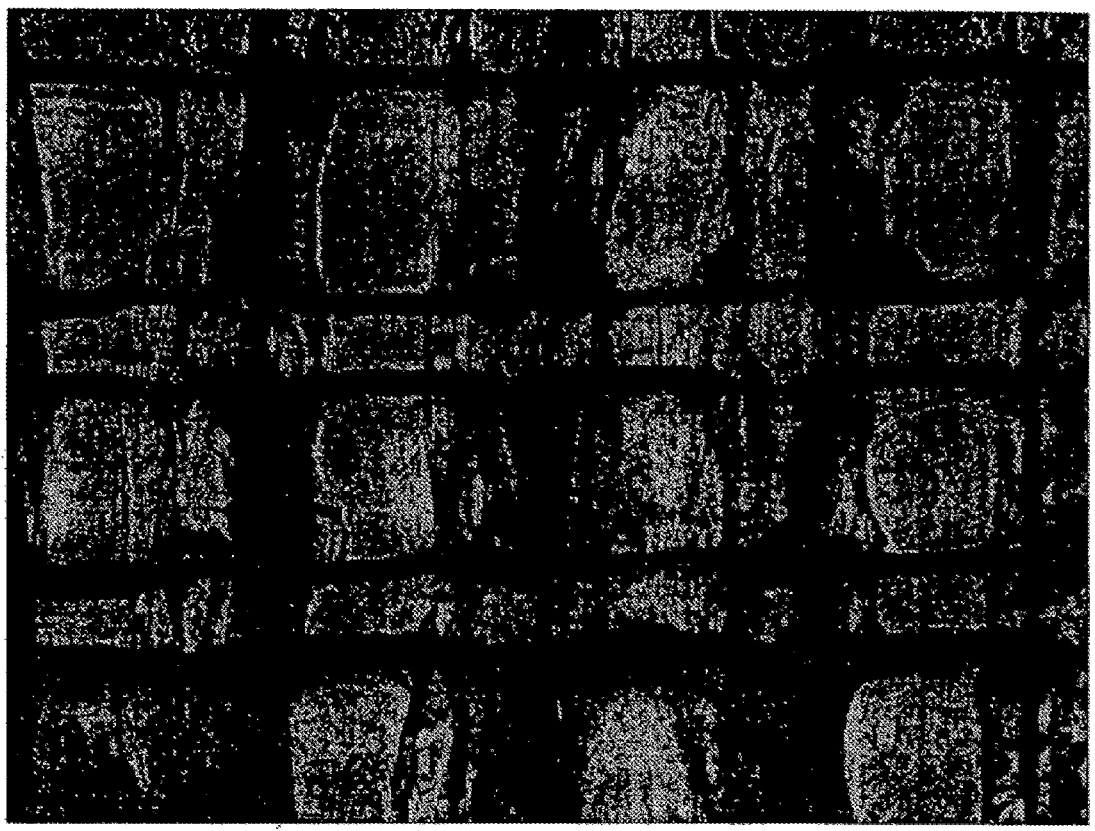
FIG. 6 shows the scaffold of Example 1 under light microscopy and demonstrates the proliferation of primary ovine fibroblast therein.
Figure 7:
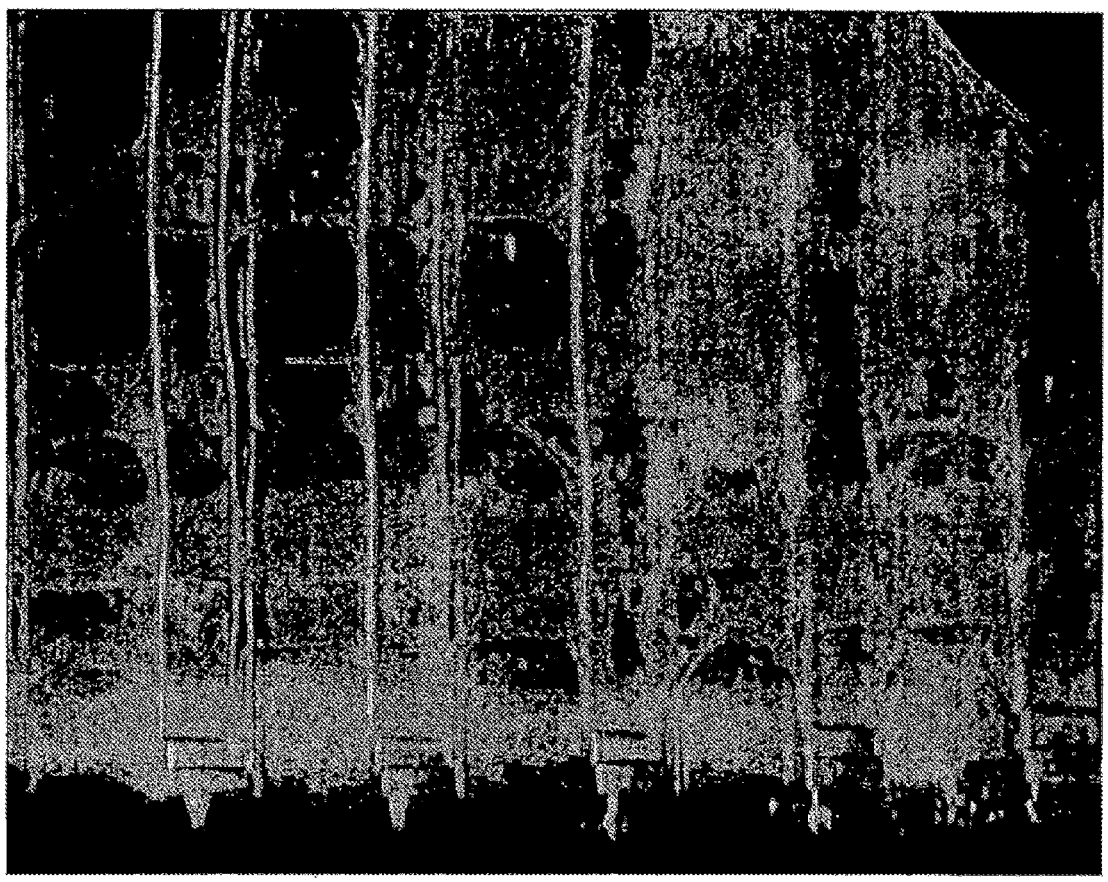
FIG. 7 shows the scaffold of Example 9 under optical microscopy after 9 weeks cell culture.
Figure 8:
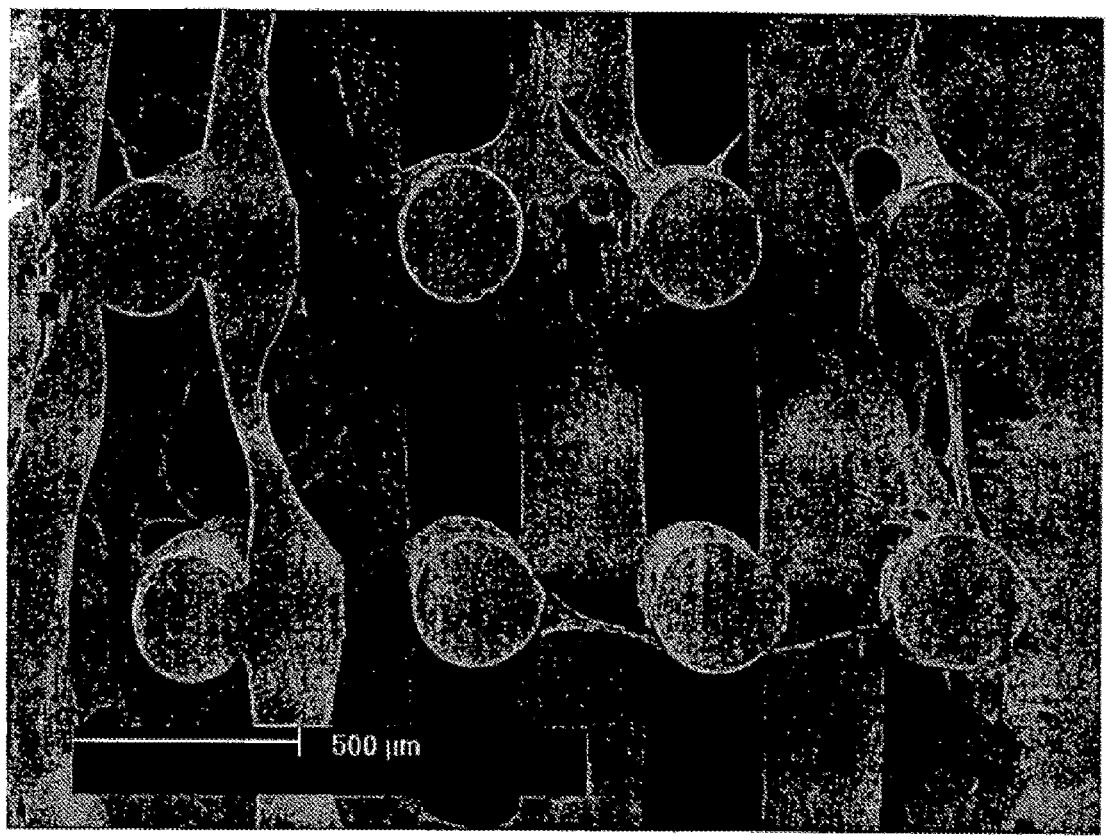
FIG. 8 shows the scaffold of Example 9 under scanning electron microscopy and demonstrates confluent cell growth.
Figure 9:
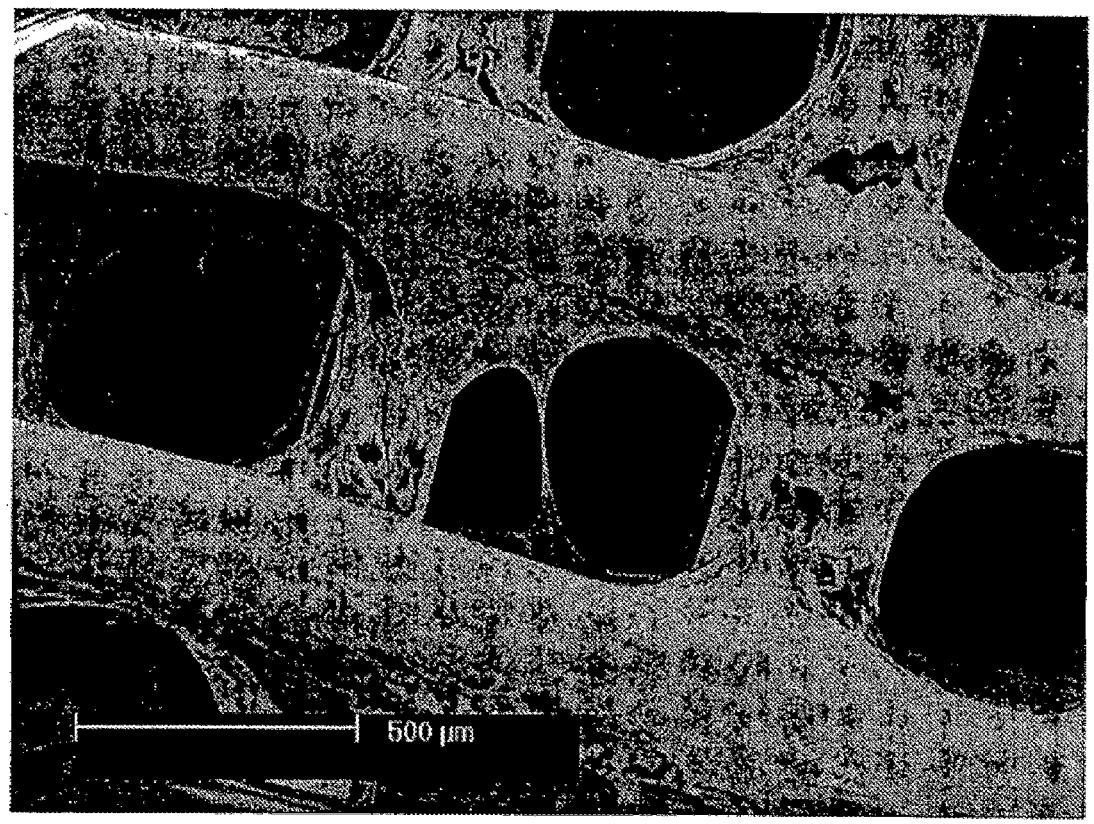
FIG. 9 shows the scaffold of Example 9 under scanning electron microscopy and demonstrates confluence and some bridging.
Figure 10:
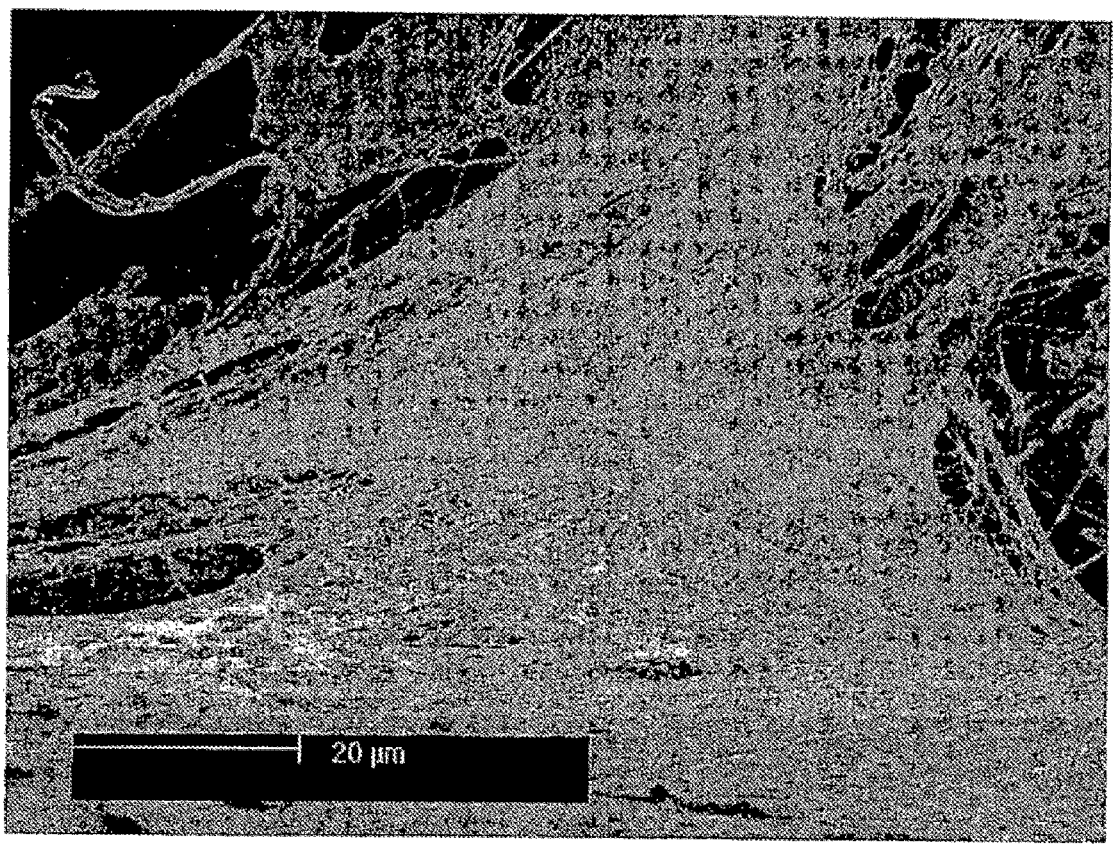
FIG. 10 shows the scaffold of Example 9 under scanning electron microscopy and demonstrates the bridging of a corner of the scaffold by cell growth.
Figure 11:
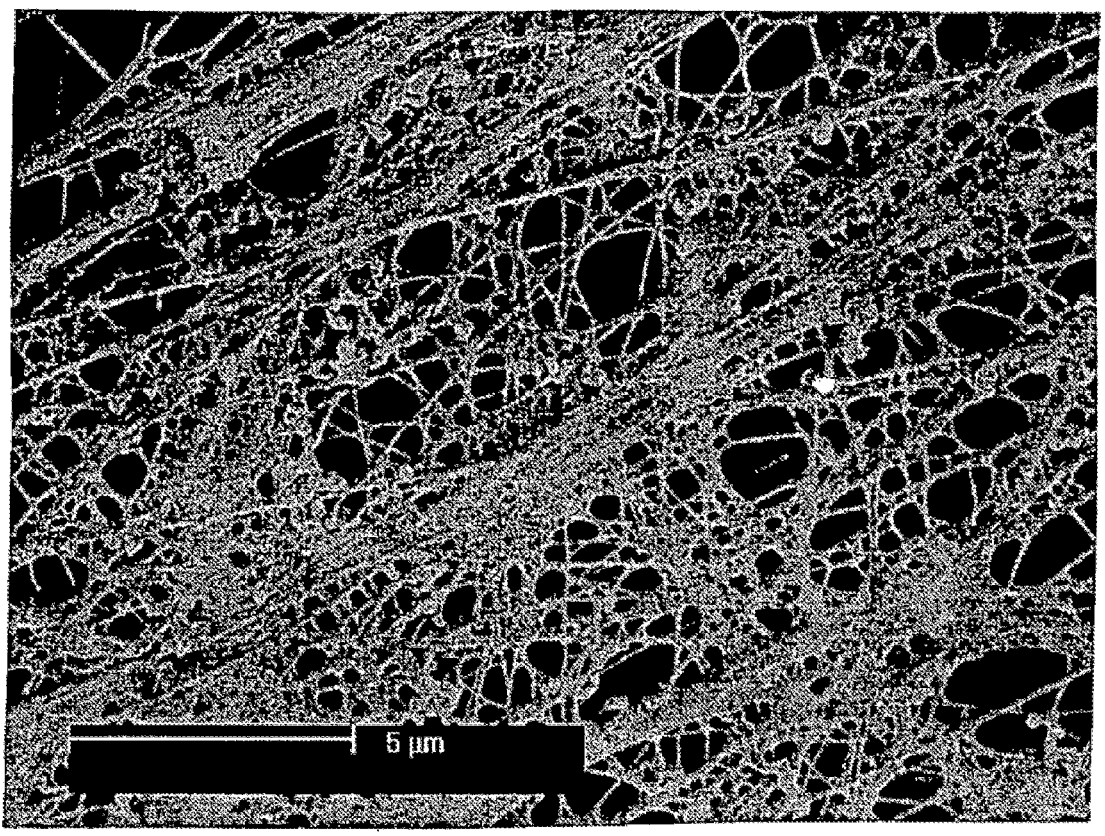
FIG. 11 shows the scaffold of Example 9 under scanning electron microscopy and shows a dose up of unsupported cells demonstrating a fibrous extra-cellular matrix.

Three dimensional scaffolds similar to those shown in FIGS. 1 to 3 were seeded with primary ovine fibroblasts explanted from the aortic heart-valve leaflet. The cells were grown in Dulbecco's Modified Eagle's Medium (DMEM) in static culture for a period of nine weeks. The temperature was 37° C. and incubator contained 5% $CO_2(g)$. The DMEM was replaced every five days. At the end of the nine weeks the scaffolds were cross linked using glutaraldehyde and then dehydrated progressively through ethanol and dried.

octoate (Aldrich) was used as received. A polyurethane composition based on a mixture of PCL diol, EG and eLDI was prepared by a one-step bulk polymerisation procedure.

A mixture of PCL diol (20.000 g) and EG (3.336 g) and stannous octoate (0.040 g) were placed in a 100 ml predried glass beaker, covered with aluminium foil and heated to 70° C. under nitrogen in a laboratory oven. ELDI (16.665 g) was weighed in a separate wet-tared predried polypropylene beaker and added to the PCL/EG/stannous octoate beaker, covered with aluminium foil and heated to 70° C. under nitrogen in a laboratory oven. ELDI was then added to the PCL/EG/stannous octoate beaker and stirred manually until gelation occurred at which time the viscous mixture was poured onto Teflon coated metal tray to cure at 100° C. for a period of about 18 hours. The resulting polymer was clear, colourless and rubbery. The molecular weight of the polymer was determined by gel permeation chromatography and the results reported in Table 3 are relative to polystyrene standards.

TABLE 3

Formulation details of various polyurethanes prepared.

| Code | Hard Segment (%) | Diisocyanate eLDI (g) | Diisocyanate HDI (g) | Chain Extenders EG (g) | Chain Extenders EG-LA (g) | Chain Extenders TETEG (g) | Soft Segments PCL 1000 (g) | Soft Segments PCL 2000 (g) | Soft Segments PEG 1000 (g) | GPC Results (in THF) Mn | GPC Results (in THF) Mw | GPC Results (in THF) PD |
|---|---|---|---|---|---|---|---|---|---|---|---|---|
| TM1-11 | 30 | 10.778 | — | 1.222 | — | — | 28.000 | — | — | 58,758 | 97,196 | 1.65 |
| TM1-9 | 50 | 16.665 | — | 3.336 | — | — | 20.000 | — | — | 94,673 | 172,649 | 1.82 |
| TM1-14 | 70 | 22.551 | — | 5.449 | — | — | 12.000 | — | — | 55,398 | 92,696 | 1.67 |
| TM1-15 | 70 | 18.587 | — | — | 9.413 | — | 12.000 | — | — | 57,847 | 115,357 | 1.99 |
| TM1-16 | 100 | 25.111 | — | — | 14.889 | — | — | — | — | 28,242 | 51,038 | 1.81 |
| TM1-22 | 50 | 15.305 | 1.266 | 3.429 | — | — | 20.000 | — | — | 56,742 | 94,031 | 1.66 |
| TM1-23 | 50 | 13.889 | 2.584 | 3.527 | — | — | 20.000 | — | — | 39,369 | 73,452 | 1.87 |
| TM1-24 | 50 | 12.846 | — | — | — | 7.154 | 20.000 | — | — | 53,266 | 96,737 | 1.82 |
| TM1-25 | 70 | 16.313 | — | — | — | 11.687 | 12.000 | — | — | 50,059 | 89,809 | 1.79 |
| TM1-27 | 33.33 | 11.759 | — | 1.574 | — | — | 13.333 | — | 13.333 | 55,398 | 97,045 | 1.75 |
| TM1-28 | 33.33 | — | 9.410 | — | 3.923 | — | 13.333 | — | 13.333 | 47,625 | 63,464 | 1.33 |
| TM1-30 | 50 | 16.665 | — | 3.335 | — | — | 10.000 | — | 10.000 | 43,770 | 72,845 | 1.66 |
| TM1-31 | 50 | 14.238 | — | — | 5.762 | — | 10.000 | — | 10.000 | 30,631 | 50,196 | 1.64 |
| TM1-29 | 50 | 16.178 | — | 3.822 | — | — | — | 20.000 | — | 59,057 | 101,750 | 1.72 |
| TM1-32 | 50 | 13.397 | — | — | 6.603 | — | — | 20.000 | — | 36,466 | 61,103 | 1.68 |

Abbreviations: eLDI: lysine diisocyanate ethyl ester, HDI: hexamethylene diisocyanate, EG-LA: ethylene glycol-lactic acid ester diol: TETEG: tetraethylene glycol, PCL: polycaprolactone diol, PEG: poly(ethylene glycol), PD: polydispersity.

SEM micrographs and optical microscopy of the cell-seeded FDM scaffolds are shown in FIGS. 7-11.

Example 10

This example illustrates the preparation of polyurethanes by varying the weight percentage of hard segment, the molecular weight of the soft segment polyol and the type of polyol. The quantities of the diisocyanate, polyol and the chain extender used are summarised in Table 3. The following example illustrates the procedure used in making sample with code TM1-9 in Table 3. Other materials in the Table were prepared accruing the same one-step polymerisation procedure.

Preparation of TM1-9 (50% Hard Segment, 50% PCL Diol 1000).

Materials: The PCL diol (molecular weight 1000) from ERA polymer Pty Ltd was dried at 90° C. for four hours under vacuum (0.1 torr). Ethylene glycol (Aldrich) was distilled and degassed at 90° C. under vacuum (0.1 torr) for three hours. Ethyl-LDI was distilled before use. Stannous

Example 11

Use as Stent Coatings

This example illustrates that the polymers could be easily dissolved in solvents such as tetrahydrofuran and coated on stainless steel surfaces.

The polymers TM1-9, TM1-11, TM1-14, TM1-15 and TM1-16 were dissolved separately in tetrahydrofuran to make 5%, 10% and 20% solutions. The solutions were used to coat stainless steel coupons by dip-coating and by spin coating (Spin coater: Model WS-400B-6NPP/Lite, Laurell Technologies Corporation). The coatings adhered well to the stainless steel showing their suitability for coating metallic surfaces. These polymers were also soluble in solvents such as chloroform, dichloromethane, dimethyl formamide and dimethyl acetamide.

Example 12

The following example illustrates the preparation of strands, fibres and tubes using a reactive extruder (Prism Model)

Polyurethanes were produced on a Prism 16 mm twin screw extruder of L/D=26:1 via liquid feed of the diisocyanate, polyester polyol, ethylene glycol and catalyst.

Methyl ester Lysine diisocyanate (m-LDI), polycaprolactone diol GMW ~426 (ERA 2043), chain extender ethylene glycol, and catalyst stannous 2 ethyl hexanoate were used as reagents to prepare polyurethanes with hard segment weight percentage of 65 and 95%.

The ratio of isocyanate to hydroxyl was kept at 1:1 and the catalyst loading was 0.1 wt %. The throughput rate was ~2 g/min and the reaction was controlled via extruder screw speed (for mixing control) and via the temperature settings across the 6 individual barrel sections and the dies. Materials based on 95 and 65% hard segment produced good tubes and filaments. A cross-linked polyurethane was produced using this technique by replacing 40% of the ethylene glycol with trimethylol propane in the 65% hard segment polyurethane formulation.

Example 13

15RA40: ELDI/PEG/EG/TMP –80% Hs

A cross linked polyurethane material was produced following a one-step procedure as described below.

A mixture of pre-dried (degassed) macrodiol PEG (2.5 g, MW 394.75), Ethylene glycol (18.77 g), Trimethylol propane (1.50 g, 40 mol % of EG) and catalyst Dibutyltin dilaurate (0.1 wt %) were weighed in a polypropylene beaker. The polymer mixture was then degassed at 70° C. for about an hour under a vacuum of 1 torr at 70° C. ELDI (7.10 g) was weighed in a syringe and added to the polyol mixture and stirred rapidly for about 3 minutes and then poured into a Teflon-coated metal pan and pressed under a nominal load of 8 tonn for 2 hours at 100° C. followed by further curing in a nitrogen-circulating oven 16 hours. The polymer showed maximum tensile stress (34±3 MPa), Youngs Modulus (1.0+0.2 MPa) and elongation at break 156±32%).

Example 14

A mixture of pre-dried (degassed) macrodiol PEG (10.0 g, MW 394.75); Ethylene glycol (7.17 g) and catalyst Dibutyltin dilaurate (0.1 wt %) was weighed in a polypropylene beaker. The polymer mixture was then degassed at 70° C. for about an hour under a vacuum of 1 torr at 70° C. ELDI (32.82 g) was weighed in a syringe and added to the polyol mixture and stirred rapidly for about 3 minutes and then poured into a Teflon-coated metal pan and pressed under a nominal load of 8 tonne for 2 hours at 100° C. followed by further curing in a nitrogen-circulating oven 16 hours. GPC showed molecular weight (MP) 112,000 and had maximum tensile stress (10±0.5 MPa), Young's Modulus (3.7+0.4 MPa) and elongation at break 301±6%).

The invention claimed is:

1. A tissue engineering scaffold comprising a cured polyurethane or polyurethane/urea,
wherein said polyurethane or polyurethane/urea comprises the reaction product of isocyanate, polyol, a chain extender having a hydrolysable linking group and, optionally, a conventional chain extender,
said polyol having a molecular weight of 120 to less than 400,
said chain extender having a hydrolysable linking group selected from the group consisting of diols and dithiols,
the acid number of the polyurethane or polyurethane/urea is about zero, and
the tissue engineering scaffold is biocompatible and biodegradable,
wherein the polyurethane or polyurethane/urea comprises hard and soft segments and the amount of hard segment is 20 to 70% by weight based on the total weight of the polyurethane or polyurethane/urea; and
wherein the soft segment comprises said polyol.

2. A scaffold according to claim 1 wherein said isocyanate is selected from the group consisting of lysine diisocyanate methyl ester, lysine diisocyanate ethyl ester, butane diisocyanate, hexamethylene diisocyanate and 4,4'-methylenebis (cyclohexylisocyanate).

3. A scaffold according to claim 1 wherein said polyol is of the formula:

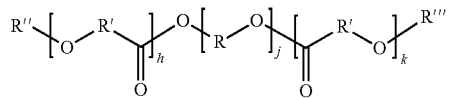

wherein h and/or k can equal 0 or are integers as is j and R" and R''' independently of each other are hydrogen, hydroxy alkyl, aminoalkyl (both primary and secondary) or carboxy alkyl and R and R' cannot be hydrogen, but can be a linear or branched alkyl, alkenyl, aminoalkyl, alkoxy or aryl.

4. A scaffold according to claim 3 wherein said polyol is selected from the group consisting of polyglycolic acid, poly (lactic acid) diol, poly (ε-caprolactone) diol and polyethylene glycol.

5. A scaffold according to claim 3, wherein each occurrence of R' is the same.

6. A scaffold according to claim 1 wherein said isocyanate is selected from the group consisting of lysine diisocyanate ethyl ester and hexamethylene diisocyanate; the chain extender having a hydrolysable linking group is ethylene glycol-lactic acid diol; and said polyol is selected from the group consisting of poly (ε-caprolactone) diol and polyethylene glycol.

7. A scaffold according to claim 3, wherein said polyol comprises a monomer selected from the group consisting of lactic acid, glycolic acid, caprolactone, ethylene glycol, propylene glycol, 4-hydroxybutyrate, 3-hydroxybutyrate, and mixtures thereof.

8. A scaffold according to claim 1, further comprising cells and/or growth factors.

9. A scaffold according to claim 8, wherein the cells are progenitor cells.

10. A scaffold according to claim 1, further comprising pharmaceuticals for use in drug delivery.

11. A scaffold according to claim 1, further comprising drugs.

12. A scaffold according to claim 1 which is a stent or stent coating.

13. A scaffold according to claim 1, further comprising pore sizes in a range of 100-500 microns.

14. A scaffold according to claim 1, further comprising a compressive strength of 0.05-100 MPA.

15. A scaffold according to claim 1, further comprising biological and/or inorganic components selected for their ability to aid tissue repair in vivo or to create physical characteristics for rapid prototyping purposes.

16. The scaffold according to claim 1, which is an in vivo tissue engineering scaffold.

17. A method of repairing tissue comprising inserting into a patient in need of tissue repair a scaffold according to claim 1.

* * * * *